United States Patent
Donaldson (10) Patent No.: US 9,402,740 B1
(45) Date of Patent: Aug. 2, 2016

(54) INTERVERTEBRAL IMPLANT HAVING MECHANICAL SECUREMENT

(71) Applicant: Jill Donaldson, Indianapolis, IN (US)

(72) Inventor: Jill Donaldson, Indianapolis, IN (US)

(73) Assignee: JWD Products, LLC, Indianapolis, IN (US)

( * ) Notice: Subject to any disclaimer, the term of this patent is extended or adjusted under 35 U.S.C. 154(b) by 0 days.

(21) Appl. No.: 14/636,305

(22) Filed: Mar. 3, 2015

(51) Int. Cl.
*A61F 2/44* (2006.01)
*A61F 2/46* (2006.01)
A61F 2/30 (2006.01)

(52) U.S. Cl.
CPC .............. *A61F 2/447* (2013.01); *A61F 2/4611* (2013.01); *A61F 2002/30579* (2013.01); *A61F 2002/4619* (2013.01); *A61F 2310/00011* (2013.01)

(58) Field of Classification Search
CPC ............................ A61F 2/442; A61F 2/4425
USPC ................. 606/246–249; 623/17.11–17.16
See application file for complete search history.

(56) References Cited

U.S. PATENT DOCUMENTS

| | | | |
|---|---|---|---|
| 7,326,248 B2 | 2/2008 | Michelson | |
| 7,846,207 B2* | 12/2010 | Lechmann | A61B 17/86 623/17.11 |
| 8,257,439 B2 | 9/2012 | Zeegers | |
| 8,257,443 B2 | 9/2012 | Kamran et al. | |
| 8,343,219 B2 | 1/2013 | Allain et al. | |
| 8,523,945 B1* | 9/2013 | Wensel | A61B 17/864 623/17.11 |
| 8,641,766 B2 | 2/2014 | Donner et al. | |
| 8,685,104 B2 | 4/2014 | Lee et al. | |
| 8,715,354 B2 | 5/2014 | Lechmann et al. | |
| 2012/0078371 A1 | 3/2012 | Gamache et al. | |
| 2012/0330424 A1 | 12/2012 | Zeegers | |
| 2013/0150968 A1 | 6/2013 | Dinville et al. | |
| 2013/0166029 A1 | 6/2013 | Dinville et al. | |
| 2013/0226300 A1 | 8/2013 | Chataigner et al. | |
| 2014/0114413 A1 | 4/2014 | Allain et al. | |
| 2014/0163684 A1 | 6/2014 | Donner et al. | |
| 2014/0180417 A1* | 6/2014 | Bergey | A61F 2/4455 623/17.16 |

OTHER PUBLICATIONS

Amedica. Valeo C Interbody Fusion Device. [online], [retrieved on Sep. 29, 2014]. Retrieved from the Internet <URL:http://www.amedica.com/product_types/valeo_interbody_fusion_devices/valeo_c_interbody_fusion_device/>.
Biomet. Solitaire Anterior Spinal System. [online], [retrieved on Sep. 29, 2014]. Retrieved from the Internet <URL:http://www.biomet.com/spine/products.cfm?pdid=3&majcid=14&prodid=220>.
DePuy Synthes, ACIS Anterior Cervical Interbody Spacer. [online], [retrieved on Sep. 29, 2014]. Retrieved from the Internet <URL:https://www.depuysynthes.com/hcp/spine/products/qs/ACIS-Anterior-Cervical-Interbody-Spacer>.

(Continued)

*Primary Examiner* — Ellen C Hammond
*Assistant Examiner* — Christina Negrellirodrigue
(74) *Attorney, Agent, or Firm* — Woodard, Emhardt, Moriarty, McNett & Henry LLP (57) ABSTRACT

An intervertebral implant for implantation between an upper vertebral body and a lower vertebral body is disclosed. It includes a body portion through which a first and second pathway pass. A first arcuate anchor is movable in an arcuate path through the first pathway and a second arcuate anchor is movable in an arcuate path through the second pathway. A locking member is movable between an open position and a closed position to either block or allow the withdrawal of the first and second arcuate anchors.

25 Claims, 7 Drawing Sheets

(56) References Cited

OTHER PUBLICATIONS

LDR Global Home. VerteBRIDGE Plating Technology. [online], [retrieved on Sep. 29, 2014]. Retrieved from the Internet <URL:http://www.ldr.com/products/vertebridge>.

Stryker. Stryker AVS Anchor-C Cervical Cage System. [online], [retrieved on Sep. 29, 2014]. Retrieved from the Internet <URL:http://www.stryker com/en-us/products/Spine/Cervical/Anchor-C/index.htm>.

* cited by examiner

INTERVERTEBRAL IMPLANT HAVING MECHANICAL SECUREMENT

BACKGROUND

The present invention relates to intervertebral implants for implantation between vertebral bodies.

Intervertebral implants are placed between vertebral bodies to replace degenerated intervertebral discs. They can be used as an alternative to spinal fusion to reduce pain in the neck and back while still allowing motion in the spine. Many intervertebral implants are designed to be fit between vertebral bodies but are not easily removable. Removal often involves destruction of the implant, so it may not be reused if removed from the spine. It would be desirable for an intervertebral implant to allow easy removal from the spine and for the implant to be reusable once removed.

Thus, there is a need for improvement in this field.

SUMMARY

The claims, and only the claims, recite the invention. In summary, it may include an intervertebral implant for implantation between an upper vertebral body and a lower vertebral body. The implant includes a body portion having a top side for contact with the upper vertebral body, a bottom side for contact with the lower vertebral body, and an anterior side between said top and bottom sides. The body portion defines in space a Z-axis generally in a cranial-caudal orientation therethrough and a Y-axis perpendicular to said Z-axis and passing through said anterior side.

The implant includes a first pathway through the body portion and a first arcuate anchor movable in an arcuate path through the first pathway to penetrate into the upper vertebral body. It also includes a second pathway through the body portion and a second arcuate anchor movable in an arcuate path through the second pathway to penetrate into the lower vertebral body.

The implant may include a locking member that is selectively movable between an open position and a closed position in a movement path that is generally transverse to the Y-axis. When the locking member is moved to the closed position it is located anteriorly of the first arcuate anchor and the second arcuate anchor, blocking their withdrawal from the anterior side of body portion. The locking member is selectively movable along a generally transverse movement path from the closed position to the open position to allow withdrawal of the first arcuate anchor and the second arcuate anchor from the anterior side of body portion to facilitate removal of the body portion from between the upper and lower vertebral bodies.

Further forms, objects, features, aspects, benefits, advantages, and embodiments of the present invention will become apparent from a detailed description and drawings provided herewith.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

With reference to the drawing Figures, for example FIGS. 1-5C, an intervertebral implant 100 for implantation between an upper vertebral body 105 and a lower vertebral body 110 is shown. The intervertebral implant 100 includes a body portion 120 having a top side 122 for contact with the upper vertebral body 105 and a bottom side 124 for contact with the lower vertebral body 110. The intervertebral implant 100 also includes an anterior side 126 between the top and bottom sides 122, 124. The body portion 120 defines, in space, a Z-axis generally in a cranial-caudal orientation therethrough and a Y-axis perpendicular to the Z-axis and passing through the anterior side 126.

Figure 1:
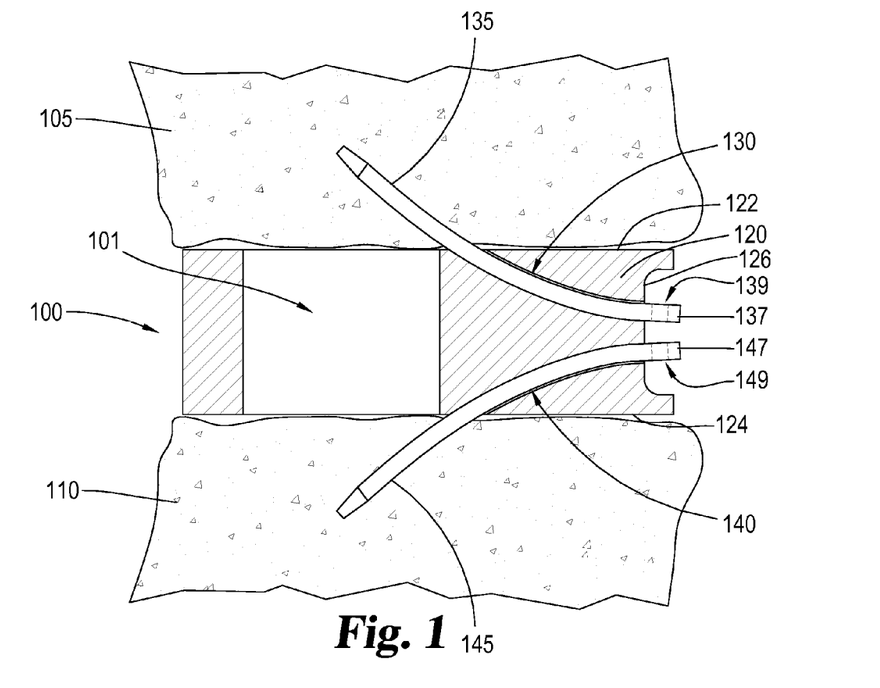
FIG. 1 is a cross-sectional view (see cut line 1-1 in FIG. 3A) of an intervertebral implant for implantation between an upper vertebral body and a lower vertebral body.
Figure 2:
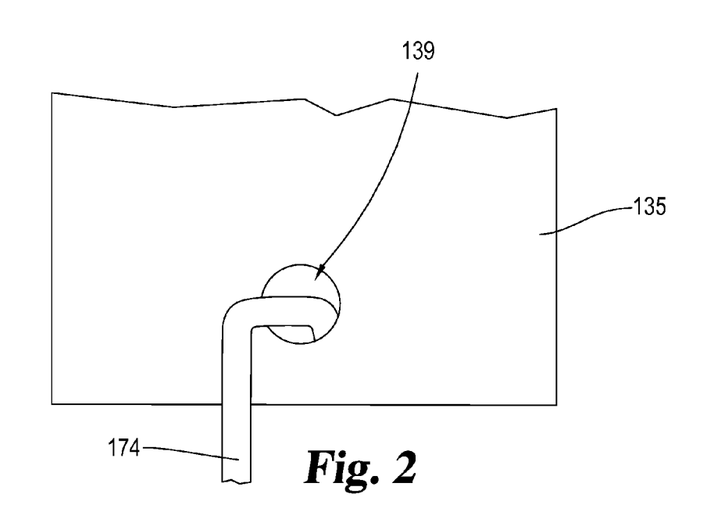
FIG. 2 is a partial top plan view of the body portion of FIG. 1 showing an opening used for removal.
Figure 3A:
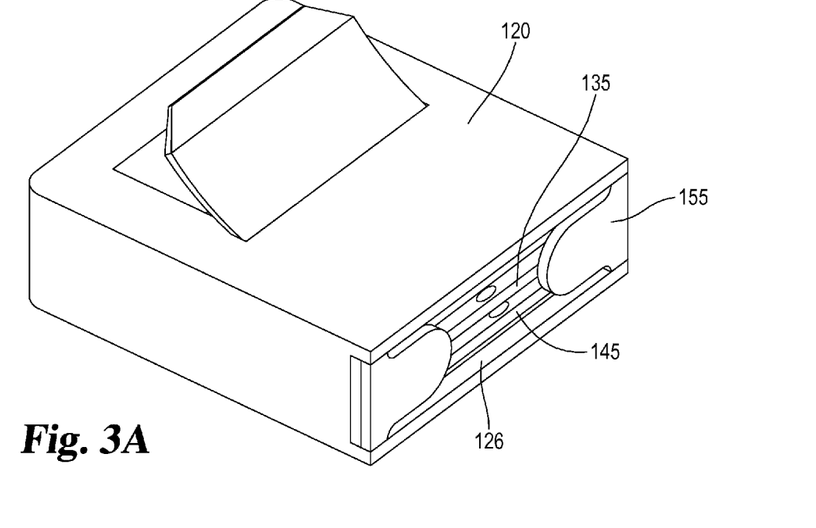
FIG. 3A is a perspective view of an intervertebral implant including a locking member comprising a gate.
Figure 3B:
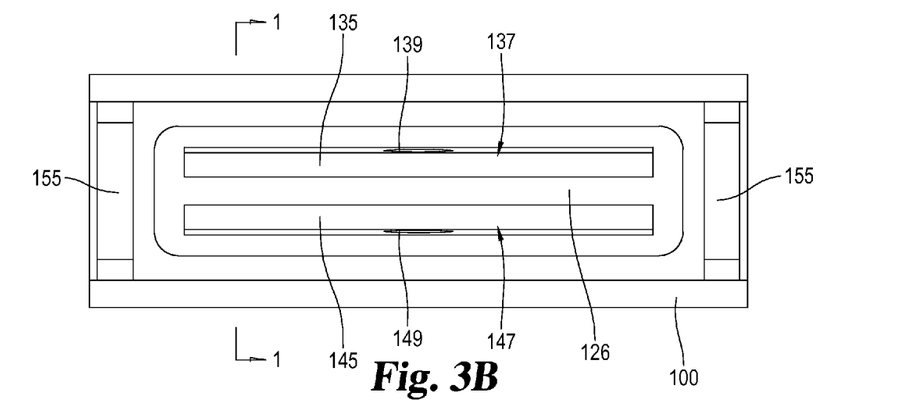
FIG. 3B is a front view of the intervertebral implant of FIG. 3A configured in an unlocked position.
Figure 3C:
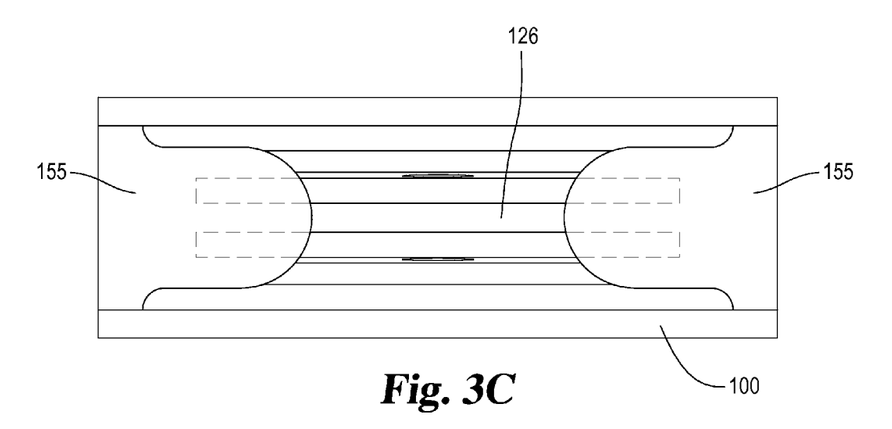
FIG. 3C is a front view of the intervertebral implant of FIG. 3A with the locking member configured in a locked position.
Figure 3D:
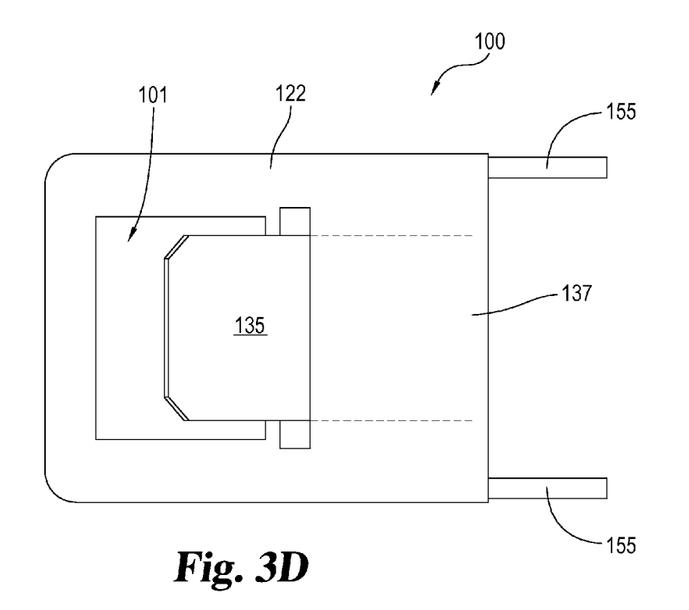
FIG. 3D is a top plan view of the intervertebral implant of FIG. 3B.
Figure 4A:
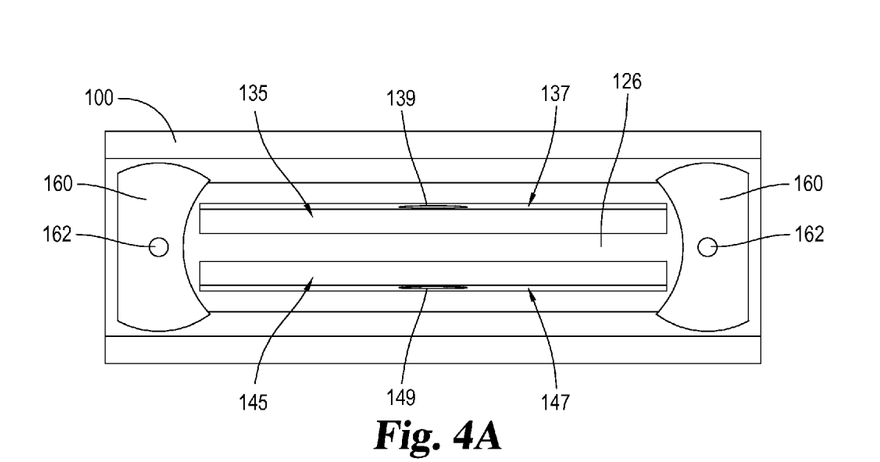
FIG. 4A is a front view of an intervertebral implant including a locking member comprising a cam configured in an unlocked position.
Figure 4B:
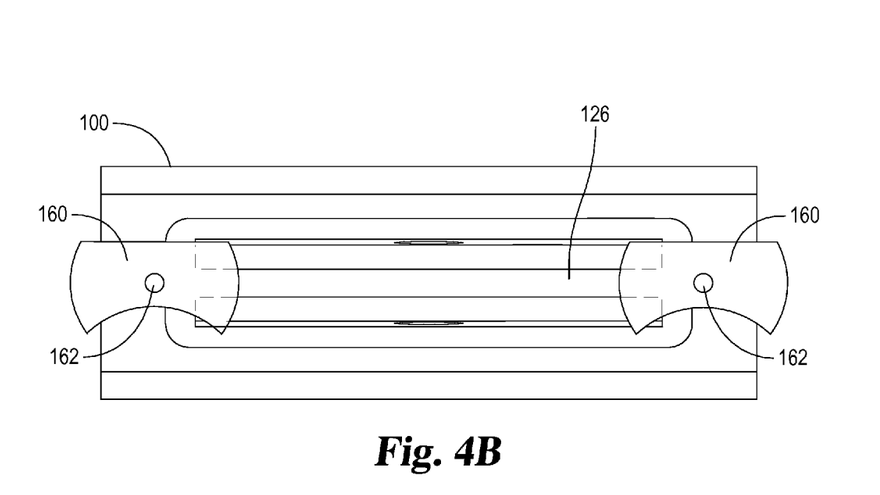
FIG. 4B is a front view of the intervertebral implant of FIG. 4A with the locking member configured in a locked position.
Figure 4C:
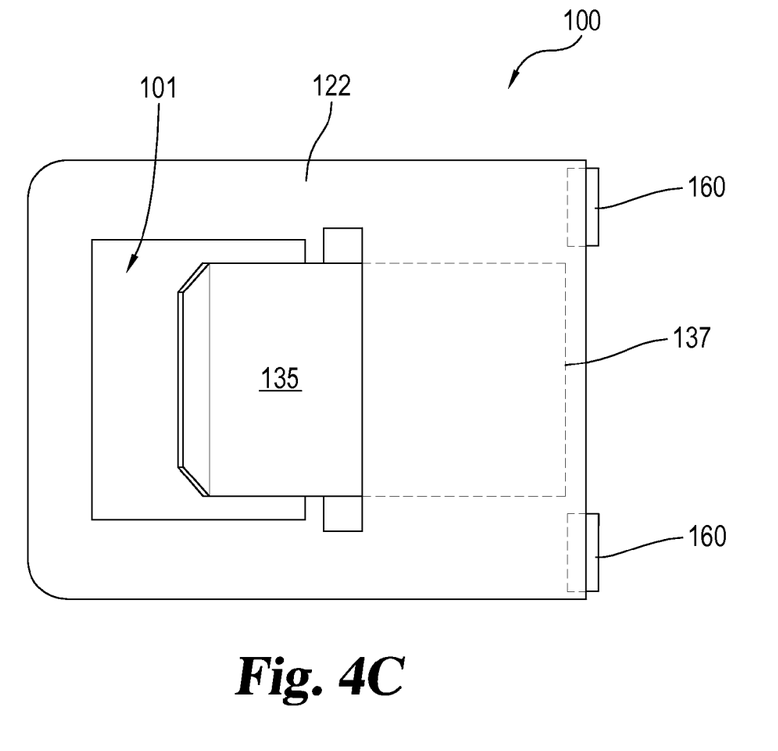
FIG. 4C is a top plan view of the intervertebral implant of FIG. 4A.
Figure 5A:
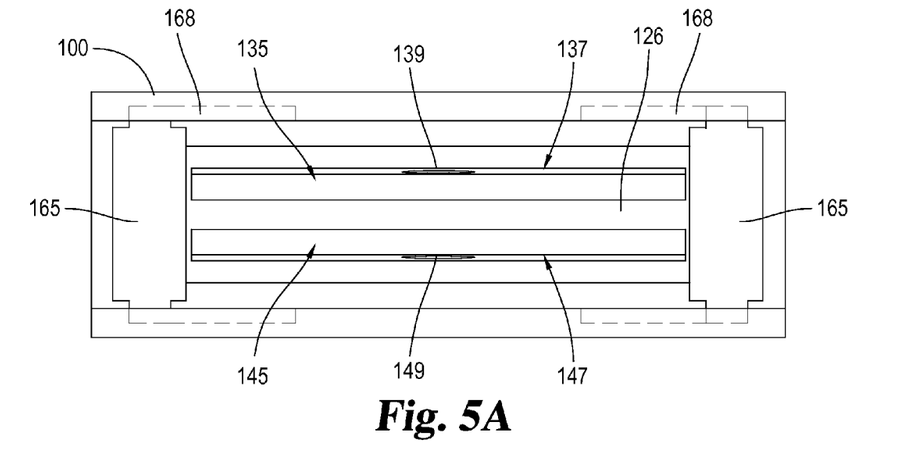
FIG. 5A is a front view of an intervertebral implant including a locking member comprising a lateral slide configured in an unlocked position.
Figure 5B:
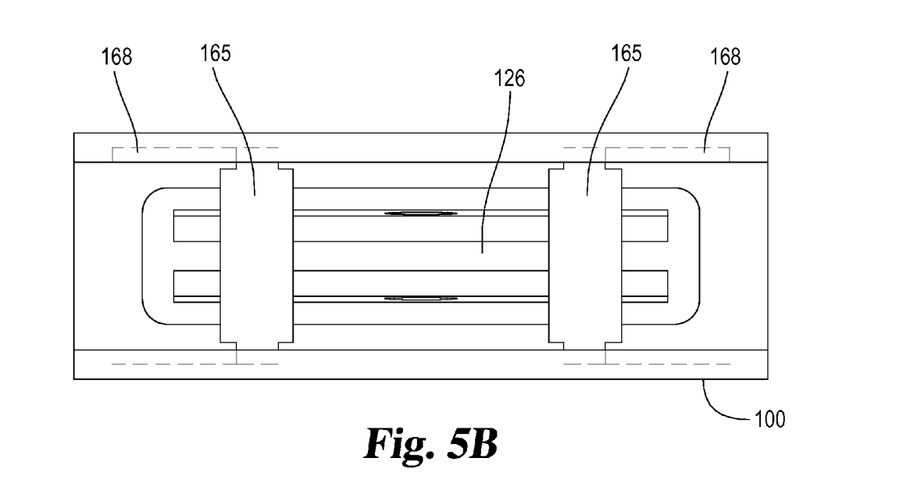
FIG. 5B is a front view of the intervertebral implant of FIG. 4A with the locking member configured in a locked position.
Figure 5C:
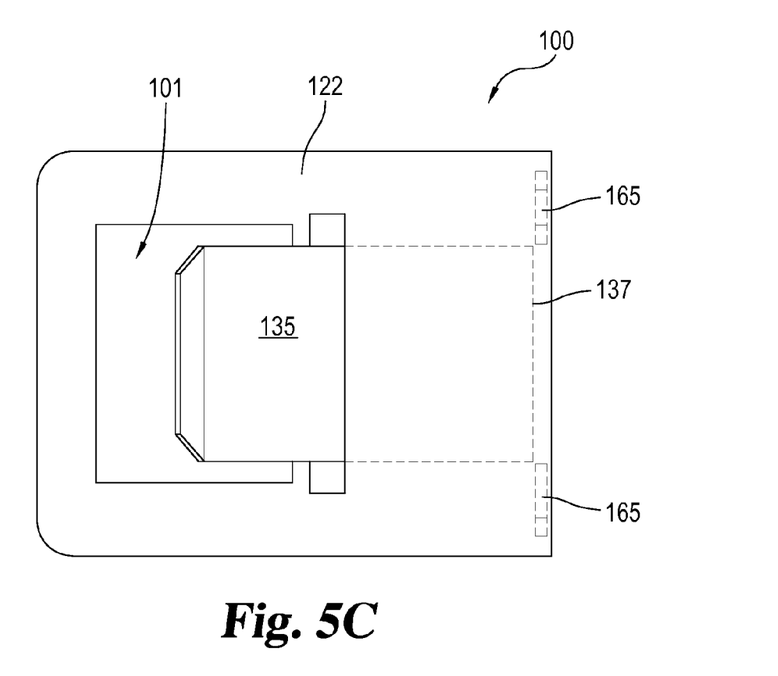
FIG. 5C is a top plan view of the intervertebral implant of FIG. 5A.

A first pathway 130 extends through the body portion 120 from the anterior side 126 to the top side 122 of the body portion. A first arcuate anchor 140 is movable in an arcuate path through the first pathway 130 to penetrate into the upper vertebral body 105.

A second pathway 140 extends through the body portion 120 from the anterior side 126 to the bottom side 124 of the body portion 120. A second arcuate anchor 145 is movable in an arcuate path through the second pathway 140 to penetrate into the lower vertebral body 110.

One or more locking member 155, 160, 165 is selectively movable between an open position and a closed position in a movement path that is generally transverse to the Y-axis. Upon transverse movement to the closed position, the locking member is located anteriorly of the first arcuate anchor 135 and the second arcuate anchor 145. The locking member blocks the withdrawal of the first arcuate anchor 135 and the second arcuate anchor 145 from the anterior side 126 of the body portion 120.

The locking member is selectively movable along the generally transverse movement path from the closed position to the open position to allow withdrawal of the first arcuate anchor 135 and the second arcuate anchor 145 from the anterior side 126 of the body portion 120. Withdrawal of first arcuate anchor 135 and second arcuate anchor 145 facilitates removal of the body portion from between the upper and lower vertebral bodies 105, 110.

One feature that is optional, but not required, may be that the locking member comprises a lateral gate 155 (see FIGS. 3A, 3B, 3C, and 3D), and the movement path of the locking member is with the lateral gate pivoting on a hinge axis.

One feature that is optional, but not required, may be that the locking member comprises a cam or other non-circular rotating member 160 (see FIGS. 4a and 4b), and the movement path of the locking member is with the cam 160 pivoting on a cam axis 162 which is generally parallel to the Y-axis. The cam may have a radially extended segment that, upon pivoting on the cam axis, is movable generally transverse to said Y-axis to block the first arcuate anchor 135 and the second arcuate anchor 145 from withdrawal.

One feature that is optional, but not required, may be that the locking member comprises a lateral slide 165 (see FIGS. 5a and 5b), and the movement path of the locking member is along a track 168 that is generally transverse to said Y-axis.

One feature that is optional, but not required, may be that the first arcuate anchor 135 has a first front edge 137 that extends anteriorly of a front surface along the anterior side 126 of the body portion 120 when implanted and penetrating into the upper vertebral body 105. Also the second arcuate anchor 145 has a second front edge 147 that extends anteriorly of the front surface along the anterior side 126 of the body portion 120 when implanted and penetrating into the lower vertebral body 110.

One feature that is optional, but not required, may be that the first arcuate anchor 135 includes a first means for being grabbed by a tool for anterior withdrawal from the body portion. The second arcuate anchor 145 includes a second means for being grabbed by a tool for anterior withdrawal from the body portion.

Figure 6:
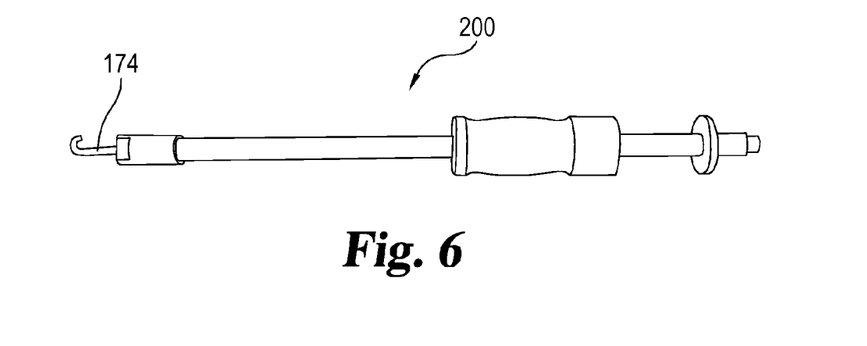
FIG. 6 is a side view of a slap hammer with a removal tool feature.

One feature that is optional, but not required, may be that the first means for being grabbed may include a first hole 139 in the first arcuate anchor 135 located near the first front edge 137. The second means for being grabbed may include a second hole 149 in the second arcuate anchor 145 located near the second front edge 147. One feature that is optional, but not required, may be that the anchor 135, 140 includes an opening 139, 149 (see FIG. 2). The openings may be configured to receive a removal tool hook 174 for removing said implant from between the upper vertebral body 105 and the lower vertebral body 110. Removal tool hook 174 may be a dedicated tool; or, optionally it may be part of another tool such as slap hammer 200 (FIG. 6). Other tools, such as pliers may be used. Optionally, however, instead of or in addition to one or more such holes, the means may include other structure, including a ridge, groove, bump, high friction surface and/or combinations thereof.

One feature that is optional, but not required, may be that the body portion 120 is made of a metallic material having a Rockwell hardness [on the A-scale] of at least 35 making it resistant to destructive implant removal.

One feature that is optional, but not required, may be that the first arcuate anchor 135 does not have a detent lock for locking it permanently in place within the first pathway 130.

Also, optionally, the second arcuate anchor 145 does not have a detent lock for locking it permanently in place within the second pathway 140.

One feature that is optional but not required is a cavity 101 (FIG. 1) for bone chips and/or other bone fusion material.

As used here (claims, specification, and other definitions) the following terms have the following meaning:

Articles and phases such as, "the", "a", "an", "at least one", and "a first", "comprising", "having" and "including" here are not limited to mean only one, but rather are inclusive and open ended to also include, optionally, two or more of such elements and/or other elements. In terms of the meaning of words or terms or phrases herein, literal differences therein are not superfluous and have different meaning, and are not to be synonymous with words or terms or phrases in the same or other claims.

The term "means for" in a claim invokes 35 U.S.C. §112(f), literally encompassing the recited function and corresponding structure and equivalents thereto. Its absence does not, unless there otherwise is insufficient structure recited for that claim element. Nothing herein or elsewhere restricts the doctrine of equivalents available to the patentee.

The term "and/or" is inclusive here, meaning "and" as well as "or". For example, "P and/or Q" encompasses, P, Q, and P with Q; and, such "P and/or Q" may include other elements as well.

The term "anchor" as used herein has the meaning, an object used to attach and secure one object to another object.

The term "anterior" as used herein has the meaning, being situated nearest or toward the front of the body. With respect to the spine, the anterior is considered to be the side of the spine closest to the stomach or the throat.

The term "anteriorly" as used herein has the meaning, positioned in a location more anterior with respect to another object where the anterior refers to a position nearer to the front of a reference point.

The term "arcuate" as used herein has the meaning, to be curved, in an arc of a circle.

The term "arcuate path" as used herein has the meaning, a track or opening used to guide movement that has a generally arcuate, or curved, shape.

The term "blocking their withdrawal" as used herein has the meaning, positioned to obstruct and disallow the removal of an object.

The term "body portion" as used herein has the meaning, the main or principal part of an object. More specifically, it refers to the part of a vertebra implant that contacts the vertebral body of a neighboring vertebra.

The term "cam" as used herein has the meaning, a rotating part that is non-circular.

The term "contact" as used herein has the meaning, of two objects the state or condition of physical touching. As used, contact requires at least one location where objects are directly or indirectly touching, with or without any other member(s) material in between.

The term "cranial-caudal orientation" as used herein has the meaning, in the direction along an axis running vertically toward and away from a (standing) patient's skull.

The term "destructive implant removal" as used herein has the meaning, removal of an implant by causing harm or damage to the implant so it may not be reused after removal.

The term "detent lock" as used herein has the meaning, a locking mechanism that includes a snap-in lock. When engaged, the releasable part prevents motion, and motion is not allowed until the part is released.

The term "facilitate" as used herein has the meaning, to aid or help accomplish an action or a process to make that action or process easier. The act of facilitation does not need to accomplish the action or process entirely on its own.

The term "front edge" as used herein has the meaning, the outer limit of an object, where the term front is used to denote the anterior-most limit of the object.

The term "front surface" as used herein has the meaning, an exterior surface which may or may not be the anterior most surface.

The term "gate" as used herein has the meaning, a structure that swings on a pivot or hinge.

The term "hinge" as used herein has the meaning, a jointed device on which a swinging part is attached so that it may rotate about the joint. The hinge may allow the part to rotate in a full circle, or rotation may be limited to an arc.

The term "hole" as used herein has the meaning, a hollow opening within a body, structure, or an object. It can be any shape.

The term "locking it permanently" as used herein has the meaning, applying a lock to a structure so that it cannot be moved. Once the lock is put in place, it cannot be removed so that motion of the structure is never allowed absent destructive implant removal.

The term "locking member" as used herein has the meaning, an object used to prevent the movement of another object or objects. For example, a locking member may be any structure used to prevent the movement of an anchor. A locking member may be fixed or may be movable.

The term "means for being grabbed by a tool" as used herein has the meaning, any structure that is configured to be able to be gripped or seized or hooked by a tool. The structure may be a portion of, or connected to a larger structure. It may include holes, ridge, bumps, grooves, and high friction surfacing.

The term "pathway" as used herein has the meaning, a track or an open area that is used to guide the movement of another object. A pathway may take various shapes, for example, it may be straight and/or curved.

The term "perpendicular" as used herein has the meaning, meeting at a substantially 90 degree angle. Small variations from 90 degrees within the range of acceptable tolerance limits are allowed.

The term "removal tool" as used herein has the meaning, any structure or object that may be used to assist in the removal of the implant or anchor from between vertebral bodies without causing damage to the implant. As an example, the removal tool may be a wire, pliers, or a hook structure.

The term "Rockwell hardness" as used refers to the scale commonly used to determine the hardness of a material where hardness is determined based on the depth of penetration of an indenter. The A-scale uses a 120° diamond cone indenter with a 60 kgf load.

The term "side" as used herein has the meaning, one of the faces on the surface of an object. An object can have multiple faces with a variety of orientations. For example, an object may have a front side, a bottom side, a back side, or a top side.

The term "slide" as used herein has the meaning, a structure that is able to move along the surface, track or grove of another object.

The term "track" as used herein has the meaning, a path or a route that defines the movement of an object. When an object is on a track, the movement of that object is confined to the position of the track.

The term "transverse" as used herein has the meaning, situated or extending across an object or an axis.

The term "vertebral body" as used herein has the meaning, the largest, cylindrical part of a vertebra. The vertebra is a bone or object that forms part of the spinal column. The vertebral body could be composed of bone or it can be an implant formed from any variety of materials that would be useful to replace bone such as titanium, stainless steel, or other metallic or non-metallic compounds.

The term "withdrawal" as used herein has the meaning, the action of removing or taking away something for a particular location.

The term "Y-axis" as used herein has the meaning, a central line of a body orientated in the Y-direction. As used in this application with respect to the human body, the Y-direction is perpendicular to the Z-axis passing through the anterior side of the vertebral implant, for example, from the stomach to the back.

The term "Z-axis" as used herein has the meaning, a central line of a body orientated in the Z-direction. As used in this application with respect to the human body, the Z-direction follows a cranial-cradium orientation, extending from the head through the feet.

The invention may include any one or more articles or devices made by any of the claimed methods and/or may by different methods but with a claimed composition.

The language used in the claims and the written description and in the above definitions is to only have its plain and ordinary meaning, except for terms explicitly defined above. Such plain and ordinary meaning is defined here as inclusive of all consistent dictionary definitions from the most recently published (on the filing date of this document) general purpose Webster's dictionaries and Random House dictionaries.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. An intervertebral implant for implantation between an upper vertebral body and a lower vertebral body, comprising:
    a body portion having a top side for contact with the upper vertebral body and a bottom side for contact with the lower vertebral body and an anterior side between said top and bottom sides, wherein said body portion defines in space a Z-axis generally in a cranial-caudal orientation therethrough and a Y-axis perpendicular to said Z-axis and passing through said anterior side;
    a first pathway through said body portion, said first pathway from said anterior side to said top side of said body portion;
    a first arcuate anchor movable in an arcuate path through said first pathway to penetrate into the upper vertebral body;
    a second pathway through said body portion, said second pathway from said anterior side to said bottom side of said body portion;
    a second arcuate anchor movable in an arcuate path through said second pathway to penetrate into the lower vertebral body;
    a locking member, said locking member selectively movable between an open position and a closed position in a movement path that is generally transverse to said Y-axis, wherein upon said transverse movement to said closed position said locking member is located anteriorly of said first arcuate anchor and said second arcuate anchor blocking their withdrawal from said anterior side of body portion; and, wherein said locking member is selectively movable along said generally transverse movement path from said closed position to said open position to allow withdrawal of said first arcuate anchor and said second arcuate anchor from said anterior side of body portion to facilitate removal of the body portion from between the upper and lower vertebral bodies.

2. The intervertebral implant of claim 1, wherein said locking member comprises a lateral gate, and wherein said movement path is with said lateral gate pivoting on a hinge axis.

3. The intervertebral implant of claim 2 wherein,
said first arcuate anchor which, when implanted and penetrating into the upper vertebral body, has a first front edge that extends anteriorly of a front surface along said anterior side of said body portion; and,
said second arcuate anchor which, when implanted and penetrating into the lower vertebral body, has a second front edge that extends anteriorly of said front surface along said anterior side of said body portion.

4. The intervertebral implant of claim 3 wherein,
said first arcuate anchor including first means for being grabbed by a tool for anterior withdrawal from said body portion; and,
said second arcuate anchor including second means for being grabbed by a tool for anterior withdrawal from said body portion.

5. The intervertebral implant of claim 4 wherein,
said first means for being grabbed comprises a first hole in said first arcuate anchor located near said first front edge; and,
said second means for being grabbed comprises a second hole in said second arcuate anchor located near said second front edge.

6. The intervertebral implant of claim 5 wherein said body portion is made of a metallic material having a Rockwell hardness [on the A-scale] of at least 35 making it resistant to destructive implant removal.

7. The intervertebral implant of claim 6 wherein,
said first arcuate anchor does not have a detent lock for locking it permanently in place within said first pathway; and,
said second arcuate anchor does not have a detent lock for locking it permanently in place within said second pathway.

8. The intervertebral implant of claim 1, wherein said locking member comprises a lateral slide, and wherein said movement path is along a track that is generally transverse to said Y-axis.

9. The intervertebral implant of claim 1, wherein said locking member comprises a cam, and wherein said movement path is with said cam pivoting on a cam axis which is generally parallel to said Y-axis, wherein said cam has a radially extended segment that, upon pivoting on said cam axis, is movable generally transverse to said Y-axis to block said first arcuate anchor and said second arcuate anchor from withdrawal.

10. The intervertebral implant of claim 1, wherein said first anchor includes an opening, wherein said opening is configured to receive a removal tool for removing said first anchor from between the upper vertebral body and the lower vertebral body.

11. The intervertebral implant of claim 1 wherein,
said first arcuate anchor which, when implanted and penetrating into the upper vertebral body, has a first front edge that extends anteriorly of a front surface along said anterior side of said body portion; and,
said second arcuate anchor which, when implanted and penetrating into the lower vertebral body, has a second front edge that extends anteriorly of said front surface along said anterior side of said body portion.

12. The intervertebral implant of claim 11 wherein,
said first arcuate anchor including first means for being grabbed by a tool for anterior withdrawal from said body portion; and,
said second arcuate anchor including second means for being grabbed by a tool for anterior withdrawal from said body portion.

13. The intervertebral implant of claim 12 wherein,
said first means for being grabbed comprises a first hole in said first arcuate anchor located near said first front edge; and,
said second means for being grabbed comprises a second hole in said second arcuate anchor located near said second front edge.

14. The intervertebral implant of claim 1 wherein said body portion is made of a metallic material having a Rockwell hardness [on the A-scale] of at least 35 making it resistant to destructive implant removal.

15. The intervertebral implant of claim 1 wherein,
said first arcuate anchor does not have a detent lock for locking it permanently in place within said first pathway; and,
said second arcuate anchor does not have a detent lock for locking it permanently in place within said second pathway.

16. An intervertebral implant for implantation between an upper vertebral body and a lower vertebral body, comprising:
a body portion having a top side for contact with the upper vertebral body and a bottom side for contact with the lower vertebral body and an anterior side between said top and bottom sides, wherein said body portion defines in space a Z-axis generally in a cranial-caudal orientation therethrough and a Y-axis perpendicular to said Z-axis and passing through said anterior side;
a first pathway through said body portion, said first pathway from said anterior side to said top side of said body portion;
a first arcuate anchor movable in an arcuate path through said first pathway to penetrate into the upper vertebral body;
a second pathway through said body portion, said second pathway from said anterior side to said bottom side of said body portion;
a second arcuate anchor movable in an arcuate path through said second pathway to penetrate into the lower vertebral body;
said first arcuate anchor which, when implanted and penetrating into the upper vertebral body, has a first front edge that extends anteriorly of a front surface along said anterior side of said body portion, said first arcuate anchor including first means for being grabbed by a tool for anterior withdrawal from said body portion; and,
said second arcuate anchor which, when implanted and penetrating into the lower vertebral body, has a second front edge that extends anteriorly of said front surface along said anterior side of said body portion, said second arcuate anchor including second means for being grabbed by a tool for anterior withdrawal from said body portion.

17. The intervertebral implant of claim 16 wherein, said first means for being grabbed comprises a first hole in said first arcuate anchor located near said first front edge; and, said second means for being grabbed comprises a second hole in said second arcuate anchor located near said second front edge.

18. The intervertebral implant of claim 17 wherein, said first arcuate anchor does not have a detent lock for locking it permanently in place within said first pathway; and, said second arcuate anchor does not have a detent lock for locking it permanently in place within said second pathway.

19. The intervertebral implant of claim 16 and further comprising a locking member, said locking member selectively movable between an open position and a closed position, wherein said locking member blocks withdrawal of said anchor members from said anterior side of body portion.

20. The intervertebral implant of claim 19, wherein said locking member comprises a lateral gate, and wherein said movement path is with said lateral gate pivoting on a hinge axis.

21. The intervertebral implant of claim 19, wherein said locking member comprises a lateral slide, and wherein said movement path is along a track that is generally transverse to said Y-axis.

22. The intervertebral implant of claim 19, wherein said locking member comprises a cam, and wherein said movement path is with said cam pivoting on a cam axis which is generally parallel to said Y-axis, wherein said cam has a radially extended segment that, upon pivoting on said cam axis, is movable generally transverse to said Y-axis to block said first arcuate anchor and said second arcuate anchor from withdrawal.

23. The intervertebral implant of claim 19, wherein said locking member is selectively movable along said generally transverse movement path from said closed position to said open position to allow withdrawal of said first arcuate anchor and said second arcuate anchor from said anterior side of body portion to facilitate removal of the body portion from between the upper and lower vertebral bodies.

24. The intervertebral implant of claim 16, wherein said body portion includes an opening, wherein said opening is configured to receive a removal tool for removing said implant from between the upper vertebral body and the lower vertebral body.

25. The intervertebral implant of claim 16 wherein said body portion is made of a metallic material having a Rockwell hardness [on the A-scale] of at least 35 making it resistant to destructive implant removal.

* * * * *